(12) United States Patent
Ray et al.

(10) Patent No.: US 7,531,308 B2
(45) Date of Patent: May 12, 2009

(54) PROCESS FOR THE REDUCTION OF ENDOTOXINS IN A PLASMID PREPARATION USING A CARBOHYDRATE NON-IONIC DETERGENT WITH SILICA CHROMATOGRAPHY

(75) Inventors: Kevin Bernard Ray, Ballwin, MO (US); Carol Ann Kreader, Kirkwood, MO (US); Fuqiang Chen, Saint Louis, MO (US); David Eric Cutter, High Ridge, MO (US)

(73) Assignee: Sigma-Aldrich Co., St. Louis, MO (US)

( * ) Notice: Subject to any disclaimer, the term of this patent is extended or adjusted under 35 U.S.C. 154(b) by 401 days.

(21) Appl. No.: 11/108,317

(22) Filed: Apr. 18, 2005

(65) Prior Publication Data

US 2005/0245733 A1 Nov. 3, 2005

Related U.S. Application Data

(60) Provisional application No. 60/565,026, filed on Apr. 23, 2004.

(51) Int. Cl.
*C12Q 1/68* (2006.01)
*C12N 1/06* (2006.01)
*C12N 15/00* (2006.01)
*C12P 19/34* (2006.01)

(52) U.S. Cl. .................... 435/6; 435/259; 435/320.1
(58) Field of Classification Search .................. None
See application file for complete search history.

(56) References Cited

U.S. PATENT DOCUMENTS

| | | | |
|---|---|---|---|
| 4,808,314 A * | 2/1989 | Karplus et al. ............. 210/638 |
| 5,234,809 A * | 8/1993 | Boom et al. ................ 435/91.2 |
| 5,346,994 A | 9/1994 | Chomczynski | |
| 5,747,663 A | 5/1998 | Colpan et al. | |
| 5,990,301 A | 11/1999 | Colpan et al. | |
| 6,011,148 A | 1/2000 | Bussey et al. | |
| 6,194,562 B1 | 2/2001 | Smith et al. | |
| 6,297,371 B1 | 10/2001 | Colpan et al. | |
| 6,383,783 B1 * | 5/2002 | Haddad ..................... 435/91.1 |
| 6,428,703 B1 | 8/2002 | Zinn et al. | |
| 6,617,443 B2 | 9/2003 | Hendriks et al. | |
| 2003/0204077 A1 | 10/2003 | Simms | |

FOREIGN PATENT DOCUMENTS

WO WO 99/63076 * 12/1999

OTHER PUBLICATIONS

Stratagene Catalog, p. 39 (1988).*
Boyle, J.S., et al., "Inhibitory Effect of Lipopolysaccharide on Immune Response After DNA Immunization Is Route Dependent", *DNA and Cell Biology* (1998) vol. 17, No. 4, pp. 343-348.
Morrison, D.C., et al., "Endotoxins and Disease Mechanisms", *Ann. Rev. Med.* (1987) vol. 38, pp. 417-432.
Wicks, I.P., et al., "Bacterial Lipopolysaccharide Copurifies with Plasmid DNA: Implications for Animal Models and Human Gene Therapy", *Human Gene Therapy* (1995) vol. 6, pp. 317-323.
International Search Report for PCT/US05/13376 dated Mar. 10, 2006 (101500) (3 sheets).

* cited by examiner

*Primary Examiner*—Teresa E Strzelecka

(57) ABSTRACT

The present invention provides methods for the reduction of endotoxins in a plasmid preparation using a carbohydrate non-ionic detergent with silica chromatography.

16 Claims, No Drawings

PROCESS FOR THE REDUCTION OF ENDOTOXINS IN A PLASMID PREPARATION USING A CARBOHYDRATE NON-IONIC DETERGENT WITH SILICA CHROMATOGRAPHY

CROSS REFERENCE TO RELATED APPLICATIONS

This application claims priority from Provisional Application Ser. No. 60/565,026 filed on Apr. 23, 2004, which is hereby incorporated by reference in its entirety.

FIELD OF THE INVENTION

The present invention relates to methods for the reduction of endotoxins in a plasmid preparation using a carbohydrate non-ionic detergent with silica chromatography.

BACKGROUND OF THE INVENTION

The invention relates to a method for reducing endotoxin levels or removing endotoxins from biological material. The method according to the invention enables, for example, high-purity plasmid DNA to be obtained from natural sources, in particular bacterial sources.

The demand for rapid and efficient methods for obtaining high-purity plasmid DNA from biological sources is constantly increasing owing to the increasing importance of recombinant DNA for exogenous expression or therapeutic applications. In particular, the demand for purification methods that can also be carried out on a larger scale is also increasing.

Virtually all known methods for the purification of, in particular, relatively large amounts of plasmid DNA include a chromatographic purification step. The efficiency of this step generally also determines the efficiency and effectiveness of the purification.

Plasmids are epigenomic circular DNA molecules having a length of between 4 and 20 kB, which corresponds to a molecular weight of between $2.6 \times 10^6$ and $13.2 \times 10^6$ daltons. Even in their compact form (supercoiled), plasmid DNA molecules normally have a size of several hundred nanometers. Owing to these dimensions, they are larger than the pores of most chromatography materials. This in turn causes, inter alia, the poor binding capacities of the separating materials generally used for plasmid DNA.

A further problem in the purification of plasmid DNA is caused by the impurities from which the plasmid DNA is to be separated. These are firstly genomic DNA and RNA. Exactly like plasmid DNA, these molecules have a strongly anionic character and thus a very similar binding behavior to separating materials.

The removal of endotoxins is at least as complex. Endotoxins are lipopolysaccharides (LPSs) which are located on the outer membrane of Gram-negative host cells, such as, for example, *Escherichia coli*. During lysis of the cells, LPSs and other membrane constituents are dissolved out, in addition to the plasmid DNA. Endotoxins are present in cells in a number of approximately $3.5 \times 10^6$ copies per cell (*Escherichia Coli* and *Salmonella Typhimurium*, Cell. and Mol. Biology, J. L. Ingraham et al. Eds., 1987, ASM) and thus exceed the number of plasmid DNA molecules by a factor of more than $10^4$. For this reason and the fact that lipopolysaccharides are high molecular polyanions which tend to co-migrate with DNA on chromatographic matrices, plasmid DNA obtained from Gram-negative host cells often contains large amounts of endotoxins. These substances result in a number of undesired side reactions in further usage of the plasmid DNA (Morrison and Ryan, 1987, Ann. Rev. Med. 38, 417-432; Boyle et al. 1998, DNA and Cell Biology, 17, 343-348). If it is intended to employ the plasmid DNA for, for example, gene therapy, it is of extreme importance that, for example, inflammatory or necrotic side reactions due to the impurities do not occur. There is therefore a great demand for effective methods for reducing endotoxin concentrations to the lowest possible levels.

Known methods for reducing endotoxin levels are based on a plurality of purification steps, frequently using silica supports, glass powder or hydroxyapatite, and on reverse-phase, affinity, size-exclusion and/or anion-exchange chromatography, and are lengthy and tedious.

Firstly, the host cells are digested by known methods, such as, for example, alkaline lysis. However, other lysis methods, such as, for example, the use of high pressure, boiling lysis, the use of detergents or digestion by lysozyme, are also known. The resultant alkaline lysate is neutralized and then centrifuged or filtered to remove any precipitate.

The plasmid DNA in the medium obtained in this way, a "cleared lysate", is principally contaminated by relatively small cell constituents, chemicals from the preceding treatment steps, RNA, proteins and endotoxins. The removal of these impurities usually requires a plurality of subsequent purification steps. Purification by means of anion-exchange chromatography has proven particularly advantageous.

However, the dynamic binding capacity of most anion exchangers for plasmid DNA is only about 0.4 mg/ml of separating material. The reason for this low value is that the functional groups are bonded to the support directly or via short spacers and consequently are only available to a limited extent for interactions with the large plasmid DNA molecules.

Another disadvantage of anion-exchange purification is that high salt is required to elute DNA from anion-exchange matrices, which requires additional steps to remove the salt for utilization of the DNA in downstream applications.

A further disadvantage of conventional anion-exchange chromatography is that a considerable amount of endotoxins is bound together with the plasmid DNA and cannot be separated off in this way. Plasmid DNA with endotoxin proportions of greater than 5000 EU/mg of plasmid DNA is often obtained. In order to reduce the endotoxin levels, further purification steps, such as, for example, chromatographic steps (gel filtration) or precipitation with isopropanol, ammonium acetate or polyethylene glycol, are therefore necessary. Purification methods which combine chromatographic methods, such as, for example, anion-exchange chromatography, and additional endotoxin removal steps, enable plasmid DNA having an endotoxin content of less than 50 EU/mg of plasmid DNA to be obtained. However, methods of this type are usually complex, time-consuming and of only limited suitability for the purification of relatively large amounts of DNA.

A method to reduce the levels of bacterial lipopolysaccharides in plasmid DNA by treatment with the detergent n-octyl-β-D-thioglucopyranoside and polymyxin-B chromatography has been described (I. P. Wicks, et al., Human Gene Therapy, 6, 317-323 (1995)).

U.S. Pat. No. 6,617,443 describes a process using a salt-free detergent solution and subsequent anion exchange chromatography to remove endotoxins from a nucleic acid preparation.

U.S. Pat. No. 5,747,663 describes a process for the removal of endotoxins from nucleic acids by pre-incubation of the nucleic acid with an aqueous salt solution and detergents, followed by treatment with anion exchange materials.

U.S. Pat. No. 5,990,301 describes a process for the purification of nucleic acids for use in gene therapy that includes treating a lysate with a non-ionic detergent followed by anion exchange.

U.S. Pat. No. 6,297,371 describes a process for the purification of nucleic acids for use in gene therapy that includes treating a lysate with a non-ionic detergent followed by anion exchange.

U.S. Pat. No. 6,194,562 describe a process for the removal of endotoxins from nucleic acids using silica-based materials, such as silica gel particles, magnetic silica particles, or diatomaceous earth.

U.S. Pat. No. 6,428,703 describes a process for purifying biological macromolecules from starting materials and for the removal of endotoxins through the use of anion exchange chromatography utilizing a polyethylene glycol non-ionic surfactant.

U.S. Pat. No. 6,011,148 describes a process for producing highly purified compositions of nucleic acids with low endotoxin levels by using tangential flow ultrafiltration.

US 2003/0204077 describes a process for the isolation of RNA from eukaryotic cells involving the use of an extraction reagent which may contain one of several non-ionic detergents.

SUMMARY OF THE INVENTION

A need however remains for an improved method for the purification of nucleic acids, in particular plasmid DNA, which provides plasmid DNA having an endotoxin content of less than about 100 EU/mg plasmid DNA. A special need exists for such a method to provide the purification of plasmid DNA with reduced endotoxin levels that is simpler and faster than existing methods. To address the continuing need for purified plasmid DNA, methods to achieve that end are herein reported. The present invention provides methods for the reduction of endotoxin levels in nucleic acid preparations using a carbohydrate non-ionic detergent in combination with silica chromatography to meet this need.

Among its several embodiments, the present invention provides a method for the reduction of endotoxin levels in nucleic acids originating from natural, genetic engineering or biotechnological biological sources, comprising the following steps:

a) preparation of a solution which comprises a medium of the nucleic acids to be purified, a binding solution and a carbohydrate non-ionic detergent;

b) application of the solution from step a) to a binding matrix;

c) washing of the binding matrix from step b) with one or more wash solutions, wherein the wash solutions comprise, alone or in combination, a binding solution, an alcohol solution and optionally a carbohydrate non-ionic detergent; and d) elution of the nucleic acids from the binding matrix of step c).

In another embodiment, the present invention further provides a kit that is suitable for use in the reduction of endotoxin levels in nucleic acids according to a method comprising the following steps:

a) preparation of a solution which comprises a medium of the nucleic acids to be purified, a binding solution and a carbohydrate non-ionic detergent;

b) application of the solution from step a) to a binding matrix;

c) washing of the binding matrix from step b) with one or more wash solutions, wherein the wash solutions comprise, alone or in combination, a binding solution, an alcohol solution and optionally a carbohydrate non-ionic detergent; and d) elution of the nucleic acids from the binding matrix of step c);

wherein the kit comprises reagents, chromatographic binding matrices for separation of nucleic acids, aqueous buffer solutions, and substances for the removal of endotoxins.

Further scope of the applicability of the present invention will become apparent from the detailed description provided below. However, it should be understood that the following detailed description and examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

Definitions

The following definitions are provided in order to aid the reader in understanding the detailed description of the present invention.

The term "chaotropic substance," as used in the present specifications, means every substance which is able to alter the secondary and/or tertiary and/or quaternary structure of a polymer without affecting the primary structure.

Examples of chaotropic substances are isothiocyanate salts, sodium iodide, sodium perchlorate, guanidinium salts, alkali salts and urea. Chaotropic substances are known to alter the secondary structure of polymers in general and/or nucleic acids in particular. This alteration can be measured in the decrease of the melting point of double stranded DNA. All kinds of nucleic acids, single stranded DNA, double stranded circular closed DNA, double stranded linear DNA and RNA can be immobilized on silica material under appropriate chaotropic conditions.

The optimal chaotropic conditions, e.g. kind and concentration of the chaotropic substance, for the immobilization of nucleic acids to silica material vary among the different species of nucleic acids. Typical binding conditions for plasmid DNA utilize 1 to 8 M solutions of guanidinium hydrochloride or guanidinium thiocyanate, displaying a pH of 4 to 7. The particular optimum depends mainly on the viscosity of the mixture, the content of proteins and other substances. In general, however, under the conditions, when circular double stranded DNA is bound, linear double stranded DNA with a similar size is also bound.

The term "substantially free of chaotropic substances" as used herein means that the concentration of chaotropic substances in the elution solution is sufficiently low that the binding matrix no longer binds the nucleic acids being purified. The concentration of chaotropic substance in the elution solution is preferably no higher than about 200 mM, more preferably no higher than about 50 mM, and most preferably is about zero. The elution solution is preferably water, more preferably deionized or distilled water, even more preferably nanopure endotoxin-free water.

The term "detergent" means an amphipathic molecule that contains both hydrophobic and hydrophilic groups. These molecules contain a polar, hydrophilic group (head) at the end of a long hydrophobic carbon chain (tail). The term "nonionic detergent" means a detergent molecule that contains an uncharged, hydrophilic head group(s). The term "carbohydrate non-ionic detergent" as used herein means an uncharged detergent molecule in which the uncharged hydrophilic head group is or is derived from a carbohydrate molecule, which includes monosaccharides, oligosaccharides and polysaccharides.

The term "alkyl" embraces linear or branched radicals having one to about twenty carbon atoms or, preferably, six to about twelve carbon atoms. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "alkylcycloalkyl" embraces radicals having one or more alkyl radicals attached to a cycloalkyl radical. The term "alkylcarbonyl" embraces an alkyl radical, as defined above, attached to a carbonyl radical. Examples of such radicals include substituted or unsubstituted n-decanoylcarbonyl and n-octanoylcarbonyl.

The term "BAC" (Bacterial Artificial Chromosome) describes a cloning vector based on bacterial mini-F plasmids.

The term "comprising" means "including the following elements but not excluding others."

Methods

Among its several embodiments, the present invention provides a method for the reduction of endotoxin levels in nucleic acids originating from natural, genetic engineering or biotechnological biological sources, comprising the following steps:

a) preparation of a solution which comprises a medium of the nucleic acids to be purified, a binding solution and a carbohydrate non-ionic detergent;

b) application of the solution from step a) to a binding matrix;

c) washing of the binding matrix from step b) with one or more wash solutions, wherein the wash solutions comprise, alone or in combination, a binding solution, an alcohol solution and optionally a carbohydrate non-ionic detergent; and d) elution of the nucleic acids from the binding matrix of step c).

In one embodiment, the biological source to be purified contains plasmid DNA.

In a further embodiment, the binding solution comprises a chaotropic substance.

In another embodiment, the chaotropic salt is preferably a guanidinium salt and even more preferably guanidinium hydrochloride.

In yet another embodiment the binding matrix is silica.

In still another embodiment, the carbohydrate non-ionic detergent is n-octyl-β-D-thioglucopyranoside.

In another embodiment, the present invention further provides a kit that is suitable for use in the reduction of endotoxin levels in nucleic acids according to a method comprising the following steps:

a) preparation of a solution which comprises a medium of the nucleic acids to be purified, a binding solution and a carbohydrate non-ionic detergent;

b) application of the solution from step a) to a binding matrix;

c) washing of the binding matrix from step b) with one or more wash solutions, wherein the wash solutions comprise, alone or in combination, a binding solution, an alcohol solution and optionally a carbohydrate non-ionic detergent; and d) elution of the nucleic acids from the binding matrix of step c);

wherein the kit comprises reagents, chromatographic binding matrices for separation of nucleic acids, aqueous buffer solutions, and substances for the removal of endotoxins.

The methods of the present invention provide one or more benefits. Utilization of a carbohydrate non-ionic detergent in combination with silica chromatography for the purification of plasmid DNA is useful as a simple and rapid method for the reduction of endotoxins. High levels of endotoxins have been shown to cause deleterious effects in downstream applications. Current methods for the preparation of plasmid DNA that contains low levels of endotoxins involve lengthy and tedious protocols that may involve difficult phase separations. Therefore the methods of the present invention provide processes that are quick and easy to perform, while retaining their efficiency to reduce endotoxins to desired levels. The non-ionic carbohydrate detergent utilized in the present invention is compatible with chaotropic substances, therefore allowing a one step process of binding plasmid DNA to a binding matrix while minimizing the absorption of endotoxins. In the final step of the methods described herein, a preferred method of elution is with a salt-free solution. This process avoids the necessity of precipitating the eluted plasmid DNA to remove salt, as other methods require. The ease of performing the present invention also decreases the risk of recontaminating the plasmid DNA with endotoxins or other impurities from the reagents added, the measuring device, or from the tube or bottle used to pellet the precipitate.

The methods of the present invention will have a number of uses. For example, the DNA purified by the methods described herein is ready for immediate use in downstream applications such as transfection, transformation, restriction digestion, ligation, sequencing and PCR. The present processes reduce the levels of endotoxins in the DNA, which can reduce transfection efficiencies in sensitive eukaryotic cell lines. The requirement for reduced levels of endotoxins is even more stringent in whole cell experiments, animal studies and human gene therapy. The presence of endotoxins in these applications can be responsible for inflammatory reactions and endotoxin shock, among other deleterious effects. The present invention provides a rapid and easy method to reduce endotoxins to a level at which they do not interfere with such sensitive applications.

The method according to the invention is particularly suitable for the purification of nucleic acids. These are single-stranded or double-stranded RNA or DNA, RNA/DNA hybrids, DNA fragments, oligonucleotides, amplified DNA or RNA, BACs, or in particular plasmid DNA. The size of the nucleic acids can be between 6 b/bp and 1000 kb/kbp.

The nucleic acids to be purified may originate from any natural, genetic engineering or biotechnological source, such as, for example, prokaryotic cell cultures. If nucleic acids from cell preparations are to be purified, the cells are firstly digested by known methods, such as, for example, lysis. If the material to be purified has already been pre-treated in another way, lytic digestion is unnecessary. For example, the medium can be obtained from biological material by removal of the cell debris and a precipitate of RNA from nucleic acid samples which have already been pre-purified and, for example, are present in buffer, or alternatively from nucleic acid solutions which have been formed after amplification and still contain endotoxin impurities. Filtration, precipitation or centrifugation steps may be necessary. The person skilled in the art is able to select a suitable digestion method depending on the source of the biological material. In any case, the sample to be purified should, for the method according to the invention, be present in a medium which does not form precipitates or cause other undesired side reactions on addition of the detergent solution. The medium is preferably a lysate obtained from cells, such as, for example, a cleared lysate.

For the purification of plasmid DNA from *E. coli*, the cells are, for example, firstly lysed by alkaline lysis with NaOH/SDS solution. Addition of an acidic potassium-containing neutralization buffer then causes the formation of a precipitate, which can be removed by centrifugation or filtration. The clear supernatant remaining, the cleared lysate, can be employed as starting material, i.e. as medium, for the method according to the invention. It is also possible firstly to concentrate or pre-purify the cleared lysate by known methods, such as dialysis or precipitation.

The medium of the nucleic acids to be purified are combined with a binding solution and a carbohydrate non-ionic detergent to form the solution described in step a) of the present invention.

The binding substance used in this step of this embodiment of this method is selected for its capacity to promote the formation of a complex between the target nucleic acid and a binding matrix. In one embodiment of this aspect of the method, the binding substance is selected for its capacity to promote a link between the silica of a silica matrix and the target nucleic acid. In such a case, the binding agent is preferably selected from the group consisting of a chaotropic substance, a salt which is not a chaotropic agent, or a combination of the above. The proportions of each binding substance used depend upon how much of each other agent is present in the resulting binding solution. When only a non-chaotropic salt, such as sodium chloride, potassium chloride, or potassium acetate is used, the concentration of salt in the binding solution is preferably at least 500 mM. Smaller concentrations of non-chaotropic salts and other binding agents can be used where more than one binding substance is present in the binding solution. When only a chaotropic substance is used, the final concentration of chaotropic substance in the binding solution is preferably at least 100 mM, more preferably at least 200 mM, and most preferably at least 500 mM. The concentration of chaotropic substance in the binding solution formed in the practice of the present method is preferably between about 0.1 M and 12 M, but more preferably between about 1 M and 10 M and even more preferably between about 4 M and 8 M. When a chaotropic substance is the only binding substance in a binding solution, the concentration of chaotropic substance therein must be sufficiently high to cause the nucleic acid to form a complex with the binding matrix, but not so high as to substantially denature, degrade, or cause the target nucleic acid to precipitate out of the binding solution. Large molecules of double-stranded DNA, such as chromosomal DNA, are stable at chaotropic agent concentrations between 0.5 and 2 M, but are known to precipitate out of solution at chaotropic substance concentrations above 2 M (see, e.g. U.S. Pat. No. 5,346,994). Contrastingly, RNA and smaller molecules of DNA such as plasmid DNA, restriction or PCR fragments of chromosomal DNA, or single-stranded DNA remain undegraded and in solution at chaotropic substance concentrations between about 2 and 8 M.

Examples of suitable chaotropic substances are chaotropic salts selected from the group consisting of a guanidinium salt, urea, an alkali thiocyanate, an alkali halide and an alkali perchlorate. Further examples of chaotropic substances for use in the present invention are sodium perchlorate, guanidine hydrochloride, guanidine isothiocyanate (also referred to as guanidine thiocyanate), sodium trichloroacetate and potassium iodide in concentrations of, for example, from about 1 to 8 M. Also useful are concentrated solutions of salts, such as, for example, greater than about 1 M NaCl, KCl, LiCl, etc., reagents such as urea (utilized at, for example, greater than about 1 M), and combinations of such components. Preferred chaotropic agents for use in promoting the formation of a complex between the target nucleic acid and the binding matrix in a preferred embodiment of the method are guanidinium salts, and more preferably guanidine hydrochloride.

The carbohydrate non-ionic detergent useful in the methods and kits of the present invention is preferably an alkyl carbohydrate non-ionic detergent. Alkyl carbohydrate non-ionic detergents useful in the present invention are carbohydrate non-ionic detergents in which one or more of the carbohydrate hydroxyl or thiol groups is attached to an alkyl, cycloalkyl, alkylcycloalkyl or alkylcarbonyl group containing at least six carbon atoms.

More preferably, the alkyl carbohydrate non-ionic detergent is selected from the group consisting of alkyl thioglucosides, alkyl glucosides, alkyl thiomaltosides, alkyl maltosides and sucrose monoalkyl esters. A preferred class of alkyl carbohydrate non-ionic detergents useful in the present invention comprises alkyl glucoside (or glucopyranoside) compounds of formula (1)

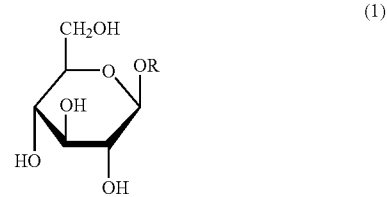

wherein R is an alkyl, cycloalkyl or alkylcycloalkyl group containing at least six carbon atoms.

Another preferred class of alkyl carbohydrate non-ionic detergents useful in the present invention comprises alkyl thioglucosides (or thioglucopyranoside) compounds of formula (2)

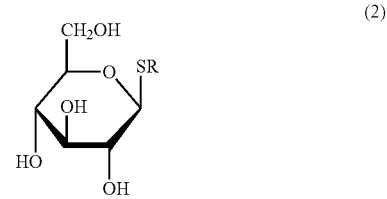

wherein R is an alkyl, cycloalkyl or alkylcycloalkyl group containing at least six carbon atoms.

Still another class of alkyl carbohydrate non-ionic detergents useful in the present invention comprises alkyl maltosides (or maltopyranoside) compounds of formula (3)

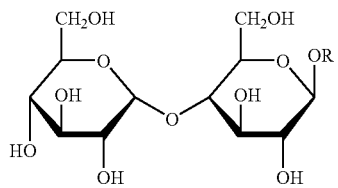

(3)

wherein R is an alkyl, cycloalkyl or alkylcycloalkyl group containing at least six carbon atoms.

Yet another class of alkyl carbohydrate non-ionic detergents useful in the present invention comprises alkyl thiomaltosides (or thiomaltopyranoside) compounds of formula (4)

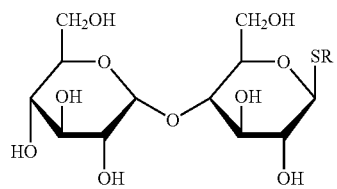

(4)

wherein R is an alkyl, cycloalkyl or alkylcycloalkyl group containing at least six carbon atoms.

The alkyl carbohydrate non-ionic detergent is even more preferably an alkyl thioglucosides and still more preferably the alkyl carbohydrate non-ionic detergent is n-octyl-β-D-thioglucopyranoside (5)

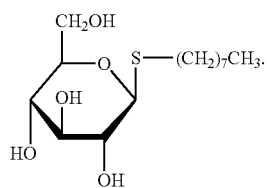

(5)

Examples of alkyl thioglucosides useful as carbohydrate non-ionic detergents in the present invention, include, but are not limited to the compounds listed in Table 1.

TABLE NO. 1

Alkyl thioglucosides.

| Name (s) | CAS Registry Number |
|---|---|
| n-Decyl-β-D-thioglucopyranoside | 98854-16-1 |
| n-Nonyl-β-D-thioglucopyranoside | 98854-15-0 |
| n-Octyl-β-D-thioglucopyranoside (OTG) | 85618-21-9 |
| n-Heptyl-β-D-thioglucopyranoside | 85618-20-8 |

Examples of alkyl glucosides useful as carbohydrate non-ionic detergents in the present invention include, but are not limited to the compounds listed in Table 2.

TABLE NO. 2

Alkyl glucosides.

| Name (s) | CAS Registry Number |
|---|---|
| n-Dodecyl-β-D-glucopyranoside | 59122-55-3 |
| n-Decyl-β-D-glucopyranoside | 58846-77-8 |
| n-Nonyl-β-D-glucopyranoside | 69984-73-2 |
| n-Octyl-β-D-glucopyranoside | 29836-26-8 |
| n-Heptyl-β-D-glucopyranoside | 78617-12-6 |
| n-Hexyl-β-D-glucopyranoside | 59080-45-4 |
| n-Octyl-α-D-glucopyranoside | 29781-80-4 |

Examples of alkyl thiomaltosides useful as carbohydrate non-ionic detergents in the present invention, include, but are not limited to the compounds listed in Table 3.

TABLE NO. 3

Alkyl thiomaltosides.

| Name (s) | CAS Registry Number |
|---|---|
| n-Decyl-β-D-thiomaltopyranoside | 148565-56-4 |
| n-Nonyl-β-D-thiomaltoside | 148565-55-3 |
| n-Octyl-β-D-thiomaltopyranoside | 148616-91-5 |

Examples of alkyl maltosides useful as carbohydrate non-ionic detergents in the present invention, include, but are not limited to the compounds listed in Table 4.

TABLE NO. 4

Alkyl maltosides.

| Name (s) | CAS Registry Number |
|---|---|
| 6-Cyclohexylhexyl-β-D-maltoside | 228579-27-9 |
| 5-Cyclohexylpentyl-β-D-maltoside | 250692-65-0 |
| Cyclohexyl-n-butyl-β-D-maltopyranoside | 181135-57-9 |
| Cyclohexyl-n-propyl-β-D-maltopyranoside | 197016-45-8 |
| 2-Cyclohexylethyl-β-D-maltoside | 260804-65-7 |
| Cyclohexylmethyl-β-D-maltoside | 260804-64-6 |
| n-Hexadecyl-β-D-maltoside | 98064-96-1 |
| n-Tetradecyl-β-D-maltoside | 18449-82-6 |
| n-Tridecyl-β-D-maltopyranoside | 93911-12-7 |
| n-Dodecyl-β-D-maltoside | 69227-93-6 |
| n-Undecyl-β-D-maltoside | 170552-39-3 |
| n-Decyl-β-D-maltopyranoside | 82494-09-5 |
| n-Nonyl-β-D-maltopyranoside | 106402-05-5 |
| n-Octyl-β-D-maltopyranoside | 82494-08-4 |

Examples of sucrose monoalkyl esters useful as carbohydrate non-ionic detergents in the present invention, include, but are not limited to the compounds listed in Table 5.

TABLE NO. 5

Sucrose monoalkyl esters.

| Name (s) | CAS Registry Number |
|---|---|
| Sucrose monodecanoate | 31835-06-0 |
| n-Monododecanoate-α-D-glucopyranoside (n-Dodecanoylsucrose) | 64395-91-1 |
| Sucrose monolaurate | 25339-99-5 |
| n-Octanoylsucrose | 42922-74-7 |

In step a) of the method of the present invention, in which a solution is prepared comprising a medium of the nucleic acids to be purified, a binding solution and a carbohydrate non-ionic detergent, the binding solution and the carbohydrate non-ionic detergent may be combined, separately or in combination, with the nucleic acids at any point in the preparation of the medium, provided that all three components are present when the above described solution is applied to a binding matrix in step b). The concentration of the carbohydrate non-ionic detergent in the solution prepared in step a) before it is applied to a binding matrix is preferably about 0.2-5.0%, more preferably about 0.4-3.0% and even more preferably about 0.6-2.0%.

Other classes of detergents, such as zwitterionic, alkyl sulfate, CHAPS, glucamide and non-ionic polyoxyethylene, do not function in the method of the present invention to provide adequate yields of nucleic acids with low levels of endotoxins. Since endotoxins are lipopolysaccharides, it is thought that the carbohydrate component of the carbohydrate non-ionic detergents claimed in the present invention solubilizes the polysaccharide portion of the endotoxin, preventing it from absorbing to the binding matrix. Thus the nucleic acids to be purified absorb to the binding matrix in the presence of the chaotropic binding solution, whereas the endotoxins do not absorb in the presence of the carbohydrate non-ionic detergent and are washed off the binding matrix column. Other classes of detergents, other than the carbohydrate non-ionic detergents claimed in the present invention, either interfere with the binding of the nucleic acids to the binding matrix, resulting in a low yield of recovered nucleic acids and/or interfere with the solubilizing of the endotoxins, resulting in high amounts of endotoxins in the final nucleic acid product. Therefore the use of a carbohydrate non-ionic detergent as described herein is essential to the method of the present invention.

The binding matrices useful in the present invention are those which bind nucleic acids in preference to endotoxins in the presence of the binding solution and the carbohydrate non-ionic detergent of step a) of the method of the present invention. Binding matrices suitable for the methods of the present invention may be inorganic, organic or a mixture, in composition.

Examples of inorganic binding matrices useful in the present invention, may be selected from the group consisting of silica, silica gel, diatomaceous earth, aluminum oxides, glass, titanium oxides, zirconium oxides and hydroxyapatite. Preferable inorganic binding matrices are, for example, porous or non-porous materials based on metal oxides and mixed metal oxides, such as those made of silica gel, silica and materials principally consisting of glass, alumina, zeolites, titanium dioxide or zirconium dioxide. More preferably, a useful binding matrix for the present invention is silica. By silica are meant $SiO_2$ crystals and other forms of silicon oxide, such as skeletons of diatoms built up from $SiO_2$, amorphous silicon oxide and glass powder.

The particle size of the inorganic binding matrix materials preferably is from about 0.1 μm to 5000 μm. If porous mineral substrates, such as, for instance, porous silica gel, porous glass, porous alumina, zeolites, are used, the pore sizes preferably are from about 100 to 5,000 nm. The substrate material can be present, for instance, in the form of loose fillings and be contacted with the solutions containing nucleic acids to be separated and purified. Preferably, however, the porous and non-porous substrate materials are in the form of filter layers arranged in some hollow body provided with an inlet and an outlet. The filter layers either consist of directed (woven) or undirected fibers made of silica, glass, quartz, ceramics, or other materials, such as minerals, or they consist of a membrane in which silica gel or silica is incorporated.

Organic binding matrices useful in the present invention may be selected, for example, from the group consisting of cellulose, dextran, agarose, anion exchange resins, acrylic amides, polystyrene resins and copolymers, thereof.

A device which may be preferably used in the method according to the invention is a hollow body, especially of cylindrical shape, provided with an inlet and an outlet. In the vicinity of the outlet, seen in the direction of flow of the solution through the hollow body, the binding matrix on which the nucleic acids are to be adsorbed is located. A means, which in an embodiment consists of two polyethylene frits arranged one above the other leaving some space between them, fixes the binding matrix, which is located in said space between the polyethylene frits, within the lumen of the hollow body. In another embodiment, the binding matrix is fixed by means of a retainer ring near the hollow body inlet. In yet another embodiment, the binding matrix is fixed by means of a retainer ring near the hollow body inlet and a polyethylene frit near the hollow body outlet. In still another embodiment, the binding matrix is fixed by means of a polyethylene frit near the hollow body inlet. The means for fixing the binding matrix may also be a self-supporting membrane in which the binding matrix is embedded. Attachment of the binding matrix or of the means fixing the binding matrix can be effected by frictional or tensional forces generated for instance by clamping the means within the hollow body and/or by fixing said means with a tension or retainer ring.

The pore size of the means, for example, polyethylene or polypropylene frits, must be large enough to allow the lysate components to pass through without obstruction. Preferably the means have pore sizes from 5 to 200 μm.

In a preferred embodiment, the binding matrix material is a reticular membrane made of silica-gel, glass or quartz fibers having pore sizes of <5 μm on which the nucleic acids are adsorbed. In an especially preferred embodiment, the binding matrix material comprises borosilicate glass microfibers from about 0.2 to 6 μm in diameter and still more preferably about 0.5 μm in diameter.

Another embodiment is represented by a device in which the mineral substrate material is a particular inorganic polymer such as silica, silica gel or quartz gel with particle sizes of from 1 to 50 μM.

The hollow body may be a commercially available tube, for instance. Between the two means being tightly pressed in, for instance polyethylene frits having pore sizes of 50 to 200 μm, there is one or more layers of a membrane having pores with sizes ranging from 0.1 to 5 μm, which membrane is made of silica, glass, quartz fibers or of silica gels. This membrane has a thickness of about 0.2 to 3.0 mm, especially of about 1.5 mm.

In a preferred embodiment of the method according to the invention, the described device in one of its embodiments, for example, is charged with the solution of the nucleic acid mixture to be separated. Then, the solution is passed through the binding matrix by suction or centrifugation or some equivalent measure as well as combinations thereof. The nucleic acids are then adsorbed on the binding matrix as long as the solution has high ionic strength (salt and/or chaotrope concentration).

According to the methods of the present invention, the binding matrix on which the nucleic acids are absorbed is then washed with one or more wash solutions, wherein the wash solutions comprise, alone or in combination, a binding solution, an alcohol solution and optionally a carbohydrate non-ionic detergent. The wash binding solution comprises a binding substance in an aqueous alcohol buffer. Preferably the binding substance is a chaotropic salt, more preferably a guanidine salt and even more preferably guanidine hydrochloride. In a preferred embodiment, the wash binding solution comprises 4.5 M guanidine hydrochloride and 100 mM Tris acetate in 25% isopropanol at pH 6.9. The wash alcohol solution comprises a low salt aqueous alcohol solution, preferably 55-85% alcohol concentration and even more preferably 60-80% alcohol concentration. In a preferred embodiment, the wash alcohol solution comprises 10 mM Tris-HCl and 10 mM NaCl in 80% ethanol at pH 8.0. In one preferred embodiment of the methods of the present invention, the nucleic acids absorbed on a binding matrix are washed sequentially with the wash binding solution followed by the wash alcohol solution.

In another preferred embodiment, the nucleic acids absorbed on a binding matrix are washed sequentially with the carbohydrate non-ionic detergent, followed by the wash binding solution, followed by the wash alcohol solution. In one especially preferred embodiment of the present invention, the carbohydrate non-ionic detergent wash comprises 1.6 M guanidine hydrochloride and 1% n-octyl-β-D-thioglucopyranoside. The addition of the optional first wash with the carbohydrate non-ionic detergent provides enhanced purification from endotoxin impurities of from about 5-fold to 25-fold lower endotoxin levels.

After the binding matrix containing the absorbed nucleic acids is washed as described in step c) of the present invention, the nucleic acids are eluted from the binding matrix using an elution buffer which is substantially free of chaotropic substances and which contains less than 200 mM salt concentration. More preferably, the nucleic acids are eluted from the binding matrix with salt-free water and even more preferably, the nucleic acids are eluted with endotoxin-free water. This method provides the desired endotoxin-free nucleic acids in a salt-free medium. Depending on the column size, large amounts of nucleic acids can be easily purified. For example, a maxi column (0.97 in diameter, 2.10 in barrel length) purifies up to about 1.2 mg of plasmid DNA, a mega column (1.47 in diameter, 6.12 in barrel length) purifies up to about 5 mg of plasmid DNA and a giga column (3.60 in diameter, 4.17 in barrel length) purifies up to about 18 mg of plasmid DNA.

According to the invention, a kit is also claimed containing components necessary for performing the methods described herein. These components include, in particular, reagents, optionally also in concentrated form for final mixing by the user, chromatographic materials for the separation of the nucleic acids, aqueous solutions (buffers, optionally also in concentrated form for final adjusting by the user), and further auxiliaries, such as substances for the removal of endotoxins, for example, a chaotropic substance and a carbohydrate non-ionic detergent. Preferably, the chaotropic substance is guanidine hydrochloride. In the kit of the present invention, the carbohydrate non-ionic detergent is preferably an alkyl carbohydrate non-ionic detergent selected from the group consisting of alkyl thioglucosides, alkyl glucosides, alkyl thiomaltosides, alkyl maltosides and sucrose monoalkyl esters. More preferably, the carbohydrate non-ionic detergent is an alkyl thioglucosides and even more preferably the carbohydrate non-ionic detergent is n-octyl-β-D-thioglucopyranoside.

In one particularly preferred embodiment, the claimed kit of the present invention comprises a silica binding matrix, guanidine hydrochloride as a chaotropic substance and n-octyl-β-D-thioglucopyranoside as a carbohydrate non-ionic detergent.

The compounds useful in the present invention can have no asymmetric carbon atoms, or, alternatively, the useful compounds can have one or more asymmetric carbon atoms. When the useful compounds have one or more asymmetric carbon atoms, they therefore include racemates and stereoisomers, such as diastereomers and enantiomers, in both pure form and in admixture. Such stereoisomers can be prepared using conventional techniques, either by reacting enantiomeric starting materials, or by separating isomers of compounds of the present invention.

Isomers may include geometric isomers, for example cis-isomers or trans-isomers across a double bond. All such isomers are contemplated among the compounds useful in the present invention.

Also included in the methods, combinations and compositions of the present invention are the isomeric forms and tautomers of the described compounds and salts thereof.

Suitable base addition salts of compounds of the present invention include metallic ion salts and organic ion salts. More preferred metallic ion salts include, but are not limited to appropriate alkali metal (group Ia) salts, alkaline earth metal (group IIa) salts and other acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, diethanolamine, and ethylenediamine. All of the above salts can be prepared by those skilled in the art by conventional means from the corresponding compound of the present invention.

The above individual references are each herein individually incorporated by reference.

The present invention is described by reference to the following Examples, which are offered by way of illustration and are not intended to limit the invention in any manner. Standard techniques well known in the art or the techniques specifically described below were utilized.

EXAMPLES

The following solutions, listed in Table 6, were used in the methods of the present invention.

TABLE NO. 6

Composition of solutions used.

| Buffer Name | Composition |
|---|---|
| Resuspension Solution | 50 mM Tris-HCl, 10 mM EDTA, 100 µg/ml RNase A, pH 8.0 |
| Lysis Solution | 1.0% SDS, 0.2 N NaOH |
| Neutralization Solution | 2M Potassium Acetate, pH 5.5 |
| Binding Solution | 5% n-octyl-β-D-thioglucopyranoside, 8M guanidine hydrochloride |
| Wash Solution 1 | 100 mM Tris Acetate, 4.5 M guanidine hydrochloride, 25% Isopropanol, pH 6.9 |
| Wash Solution 2 | 10 mM Tris-HCl, 10 mM NaCl, 80% Ethanol, pH 8.0 |
| Additional Wash Solution | 1% n-octyl-β-D-thioglucopyranoside, 1.6 M guanidine hydrochloride |

Example 1

Purification of Endotoxin-free pBICEP-CMV-1-LacZ using n-octyl-β-D-thioglucopyranoside Detergent with Silica Chromatography A flask containing LB medium and 100 μg/ml of ampicillin was inoculated with *E. coli* strain HB101 harboring pBICEP-CMV-1-LacZ. The culture was grown shaking at 250 RPM for 17 hours at 37° C. A 150 ml aliquot of the culture was harvested by centrifugation for each sample prepared. The bacterial pellets were thoroughly resuspended in 12 ml of Resuspension Solution. The cell suspensions were then subjected to a modified alkaline-SDS lysis by the addition of 12 ml of Lysis Solution. The lysates were neutralized with the addition of 12 ml of Neutralization Solution. This resulted in the formation of a white flocculent precipitate containing denatured proteins, lipids, SDS, chromosomal DNA, and other cell debris. The lysates were transferred to individual filtration units and incubated at room temperature for 5 minutes. The lysates were drawn through the filtration units by vacuum resulting in a clarified lysate.

The clarified lysates were prepared for the silica column by the addition of 9 ml of Binding Solution. The mixtures were then loaded onto their respective silica columns and drawn through by vacuum. The plasmid DNA was adsorbed onto the silica membrane while the endotoxins were prevented from binding to the matrix.

Contaminants were further removed from the columns by the addition of 12 ml of Wash Solution 1, followed by 12 ml of Wash Solution 2. The columns were allowed to dry for 10 minutes while still under vacuum. The silica columns were transferred to individual collection tubes.

Finally, the plasmid DNA was eluted by the addition of 3 ml of endotoxin-free water to each sample and centrifuging at 3,000×g for 5 minutes. The recovered eluates were then ready for analysis and use in downstream applications. All samples were successfully digested and sequenced to illustrate the quality of the samples.

For comparison purposes, plasmid samples were also prepared using a commercially available kit that utilizes silica technology and an endotoxin-free kit that utilizes anion exchange technology.

Plasmid concentrations were determined by taking absorbance readings at 260 nm. The concentrations were multiplied by the volume of the recovered eluate and plasmid recovery was reported as total yield (μg).

Endotoxin levels were determined by the QCL-1000 LAL kit from BioWhittaker with levels being reported as Endotoxin Units per mg of plasmid DNA (EU/mg). The results are shown in Table No. 7.

TABLE NO. 7

| | Results of method. | | |
|---|---|---|---|
| Purification Method (2 replicates each) | Average Plasmid Yield (μg) | Average Endotoxin Levels (EU/mg) | Approximate Time/Prep (minutes) |
| Detergent w/Silica | 1400 | 24 | 35 |
| Commercial Silica | 1600 | 160000 | 30 |
| Commercial Endo-Free Anion-Exchange | 990 | 16 | 165 |

Plasmid samples were transfected into Human Hepatoma (HuH7) cells, which are known to be sensitive to endotoxins, using Escort II Transfection Reagent from Sigma-Aldrich. β-Galactosidase activity was measured using the β-Galactosidase Reporter Gene Activity Detection Kit from Sigma-Aldrich at 48 hours post-transfection. Absorbance readings were taken at 420 nm and β-gal activity was recorded in units of β-gal/plate. The transfection results of the purified plasmid samples are shown in Table No. 8.

TABLE NO. 8

| | Transfection results of purified plasmids. |
|---|---|
| Purification Method | Transfection Efficiency (B-gal/Plate) |
| Detergent w/Silica | 182.2 ± 3.1 |
| Commercial Silica | 45.2 ± 0.7 |
| Commercial Endo-Free Anion-Exchange | 143.9 ± 5.5 |

Example 2

Further Reduction in Endotoxin Levels by Using an Additional Wash Solution Containing n-octyl-β-D-thioglucopyranoside Detergent and Guanidine Hydrochloride A flask containing LB medium and 100 μg/ml of ampicillin was inoculated with *E. coli* strain DH5α harboring pCMV-SPORT-βgal. Control samples were prepared, loaded onto the silica column, washed and eluted as described in Example 1. Additional samples were prepared and loaded onto the silica column as described in Example 1. The columns were then washed with 12 ml of 1% n-octyl-β-D-thioglucopyranoside in 1.6M guanidine hydrochloride. The columns were further washed with 12 ml of Wash Solution 1 and 12 ml of Wash Solution 2. The columns were dried and the plasmid was eluted as described in Example 1. Table No. 9 shows the reduced endotoxin levels obtained with the additional wash.

TABLE NO. 9

| | Results with additional wash. | |
|---|---|---|
| Sample (2 replicates each) | Plasmid Yield (ug) | Endotoxin Levels (EU/mg) |
| Control | 840 | 59 |
| Plus additional wash | 780 | 4 |

Example 3

Purification of pCMV-SPORT-βgal Using Various Non-Ionic Detergents with Silica Chromatography A flask containing LB medium and 100 μg/ml of ampicillin was inoculated with *E. coli* strain DH5α harboring pCMV-SPORT-βgal. The plasmid was purified as in Example 1 with the detergents listed in Table No. 10 on a reduced scale (5%). All detergent solutions were made up in 8M guanidine hydrochloride and used as the Binding Solution. Table No. 10 shows the results indicating that only carbohydrate non-ionic detergents provide good plasmid yields along with low endotoxin levels.

TABLE NO. 10

Results with various detergents.

| Detergent Class | Detergent | Average Plasmid Yield (ug) | Average Endotoxin Levels (EU/mg) |
|---|---|---|---|
| | No Detergent Control | 29 | >4500 |
| Alkyl thioglucoside | Detergent control 5% n-octyl-β-D-1-thioglucopyranoside | 22 | 32 |
| Alkyl glucoside | 2.5% n-octyl-β-D-glucopyranoside | 37 | 120 |
| | 5% n-octyl-β-D-glucopyranoside | 29 | 26 |
| Alkyl maltoside | 10% n-decyl-p-D-maltopyranoside | 16 | 58 |
| Alkyl sulfate | 0.5% sodium dodecyl sulfate | 42 | * |
| | 1.0% sodium dodecyl sulfate | 46 | 1800 |
| Zwitterionic | 0.5% SB3-14 | 6 | * |
| | 1.0% SB3-14 | 2 | 1700 |
| | 2.5% SB3-14 | 1 | * |
| | 5.0% SB3-14 | 2 | * |
| | 10.0% SB3-14 | 1 | * |
| CHAPS series | 2.5% CHAPS | 13 | >7300 |
| | 5.0% CHAPS | 6 | >14000 |
| | 10.0% CHAPS | 1 | * |
| | 2.5% CHAPSO | 11 | >8200 |
| | 5.0% CHAPSO | 7 | >13000 |
| | 10.0% CHAPSO | 2 | * |
| Glucamide | 10.0% MEGA-8 | 9 | 6000 |
| Polyoxyethylenes | 0.5% TRITON X-100 | 7 | * |
| | 1.0% TRITON X-100 | 4 | * |
| | 2.5% TRITON X-100 | 2 | 4700 |
| | 2.5% TRITON X-114 | 2 | 6400 |
| | 5.0% TRITON X-114 | 2 | * |
| | 2.5% TWEEN 20 | 2 | >6300 |
| | 5.0% TWEEN 20 | 2 | * |
| | 1.5% BRIJ 35 | 1 | >11000 |
| | 3.0% BRIJ 35 | 1 | * |

* Not tested.

Example 4

Purification of pCMV-SPORT-βgal Using Preferred Carbohydrate Non-Ionic Detergents with Silica Chromatography A flask containing LB medium and 100 μg/ml of ampicillin was inoculated with *E. coli* strain DH5α harboring pCMV-SPORT-βgal. Samples were prepared as described in Example 1. All detergent solutions were made up in 8M guanidine hydrochloride and used as the Binding Solution. Table No. 11 shows that the three different carbohydrate non-ionic detergents performed similarly, giving high plasmid yields with low endotoxin levels.

TABLE NO. 11

Results with carbohydrate non-ionic detergents.

| Detergent Class | Detergent | Average Plasmid Yield (ug) | Average Endotoxin Levels (EU/mg) |
|---|---|---|---|
| | No Detergent Control | 1300 | 1100 |
| Alkyl thioglucoside | 5% n-octyl-β-D-1-thioglucopyranoside | 1100 | 6 |
| Alkyl glucoside | 5% n-octyl-β-D-glucopyranoside | 1100 | 9 |
| Alkyl maltoside | 10% n-decyl-β-D-maltopyranoside | 1200 | 29 |

The contents of each of the references cited herein, including the contents of the references cited within these primary references, are herein incorporated by reference in their entirety.

While the invention has been described and illustrated with reference to certain particular embodiments thereof, those skilled in the art will appreciate that various changes, modifications and substitutions can be made therein without departing from the spirit and scope of the invention.

It is intended, therefore, that the invention be defined by the scope of the claims which follow and that such claims be interpreted as broadly as is reasonable.

What is claimed is:

1. A method for reducing endotoxin levels in a nucleic acid solution comprising:
    a) contacting a nucleic acid solution with a carbohydrate non-ionic detergent selected from the group consisting of alkyl thioglucosides, alkyl glucosides and alkyl maltosides;
    b) contacting the solution resulting from step a) to an inorganic binding matrix;
    c) washing the binding matrix resulting from step b) to obtain a nucleic acid composition having an endotoxin content of less than 100 EU/mg.

2. The method of claim 1, further comprising eluting the nucleic acid composition from the inorganic binding matrix of step c).

3. The method of claim 2, wherein the eluted nucleic acid composition comprises an average plasmid DNA yield of about 15 ug to about 50 ug and an average endotoxin level from about 20 EU/mg to about 100 EU/mg.

4. The method of claim 1, wherein the carbohydrate non-ionic detergent is n-octyl-β-D-thioglucopyranoside.

5. The method of claim 1, wherein the inorganic binding matrix is selected from the group consisting of silica, diatomaceous earth, aluminum oxides, glass, titanium oxides, zirconium oxides, and hydroxyapatite.

6. The method of claim 1, wherein the inorganic binding matrix is silica.

7. The method of claim 1, wherein the nucleic acid solution is a plasmid DNA solution.

8. The method of claim 1, wherein the nucleic acid solution comprises double-stranded RNA or DNA, RNA/DNA hybrids, DNA fragments, oligonucleotides, amplified DNA or RNA, BACs, plasmid DNA, or a combination thereof.

9. The method of claim 1, wherein the nucleic acid solution from step a) comprises a binding solution.

10. The method of claim 9, wherein the binding solution comprises a chaotropic substance.

11. The method of claim 10, wherein the chaotropic substance is a chaotropic salt selected from the group consisting of a guanidinium salt, urea, an alkali thiocyanate, an alkali halide, an alkali perchlorate, and a combination thereof.

12. The method of claim 11, wherein the chaotropic salt is guanidine hydrochloride.

13. The method of claim 1, wherein step c) comprises washing with a binding solution, an alcohol solution, a carbohydrate non-ionic detergent, or a combination thereof.

14. The method of claim 1, further comprising obtaining the nucleic acid solution to be used in step a) from a biological source by a digestion method.

15. The method of claim 14, wherein the digestion method comprises alkaline lysis, centrifugation, filtration or precipitation.

16. The method of claim 1, wherein the nucleic acids solution is a cleared lysate.

* * * * *